US00PP14089P39

(12) United States Plant Patent
Llanos

(10) Patent No.: US PP14,089 P3
(45) Date of Patent: Aug. 26, 2003

(54) AVOCADO TREE NAMED 'LLANOS HASS'

(76) Inventor: Anthony Phillip Llanos, deceased, late of Kwinana (AU), by Cassandra Ann Llanos, legal representative ( * ) Notice: Subject to any disclaimer, the term of this patent is extended or adjusted under 35 U.S.C. 154(b) by 20 days.

(21) Appl. No.: 09/876,599

(22) Filed: Jun. 7, 2001

(65) Prior Publication Data

US 2003/0005500 P1 Jan. 2, 2003

(51) Int. Cl.[7] ..... A01H 5/00
(52) U.S. Cl. ..... Plt./200
(58) Field of Search ..... Plt./200

(56) References Cited

PUBLICATIONS

UPOV–ROM GTITM Computer Database, 2001/06, GTI Jouve Retrieval Software, citation for 'Llanos Hass'.*

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

Described is a new Avocado variety whose fruit matures at a minimum of approximately 4 to 6 weeks earlier than the variety 'HASS'.

3 Drawing Sheets

LATIN NAME OF GENUS AND SPECIES

The present invention relates to a new *Persea americana* plant.

BACKGROUND OF THE INVENTION

Avocado plants in cultivation are mainly varieties of *Persea americana*. The new variety was developed by open pollination followed by seedling selection: an open pollinated seedling was selected at applicant's property in Kwinana, Hope Valley, Western Australia. which displayed precocious and consistent fruit, and which was an improvement to the variety 'HASS' inasmuch as it consistently matured earlier than 'HASS'. DNA profiling has shown that 'HASS' (U.S. Plant Pat. No. 139, now expired) is likely to be one of the parents of the new variety. Propagation by vegetative grafting onto rootstocks in Kwinana, Hope Valley, Western Australia has demonstrated that the characteristics of the new variety are transmitted through succeeding generations of asexual reproduction.

SUMMARY OF THE INVENTION

The present invention is a new and distinctive Avocado plant having precocious and consistent fruit set similar to that of its parent variety, 'HASS', but which matures consistently approximately 4 to 6 weeks earlier than that of its parent variety 'HASS'.

The new variety was asexually reproduced by vegetative grafting onto Guatemalan Avocado, Reed variety (not patented), seedling rootstocks and then advantageously planted in soil consisting of deep sands.

BRIEF DESCRIPTION OF ILLUSTRATION(S)

The accompanying photographic illustrations show typical specimens of the vegetative growth and flowers of the new variety in different stages of development and depicted in color as nearly true as it is reasonably possible to make the same in a color illustration of this character.

DESCRIPTION OF THE NEW VARIETY

Figure 1:
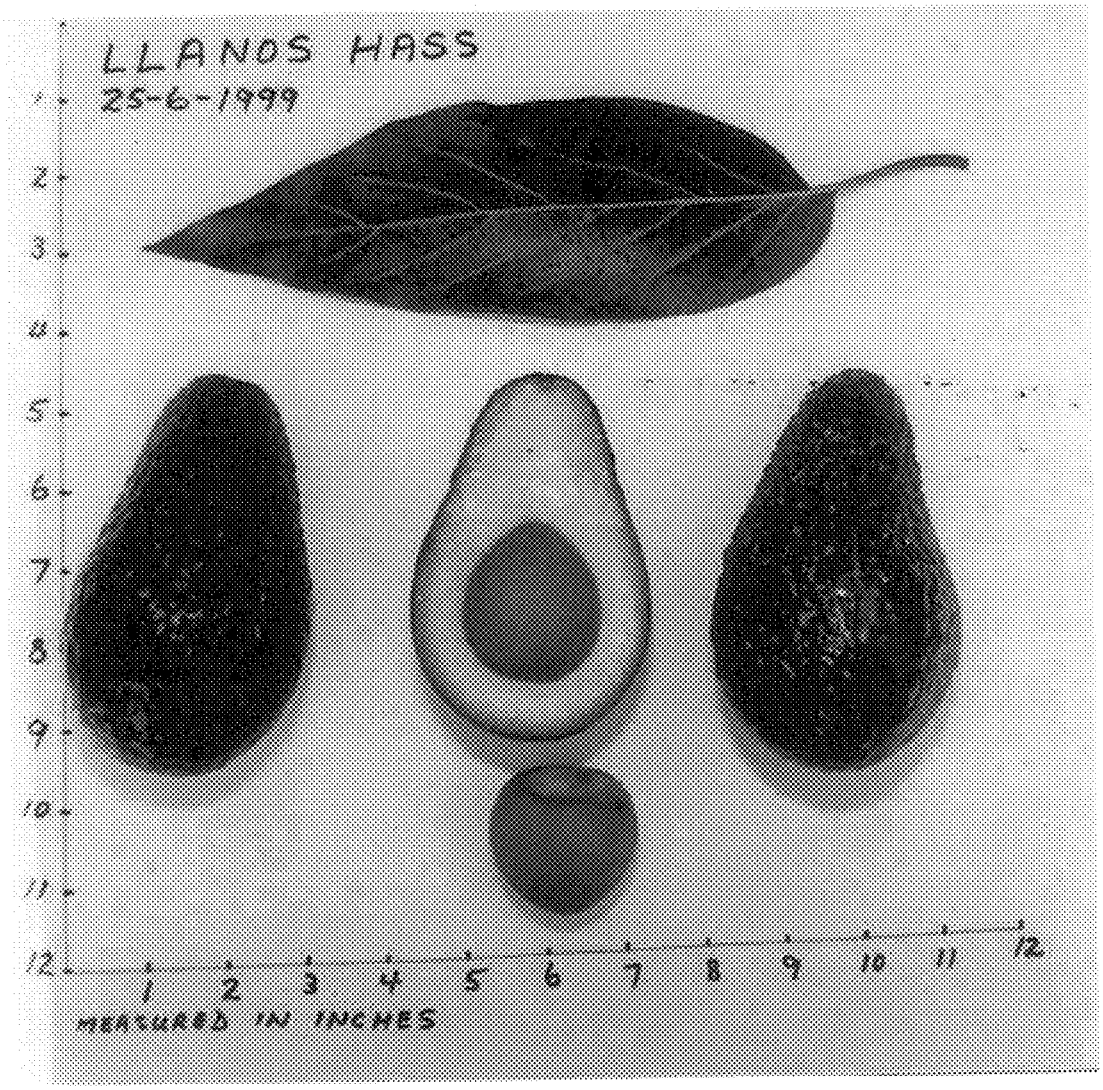
FIG. 1 shows a typical fruit and leaf of the new variety.
Figure 2:
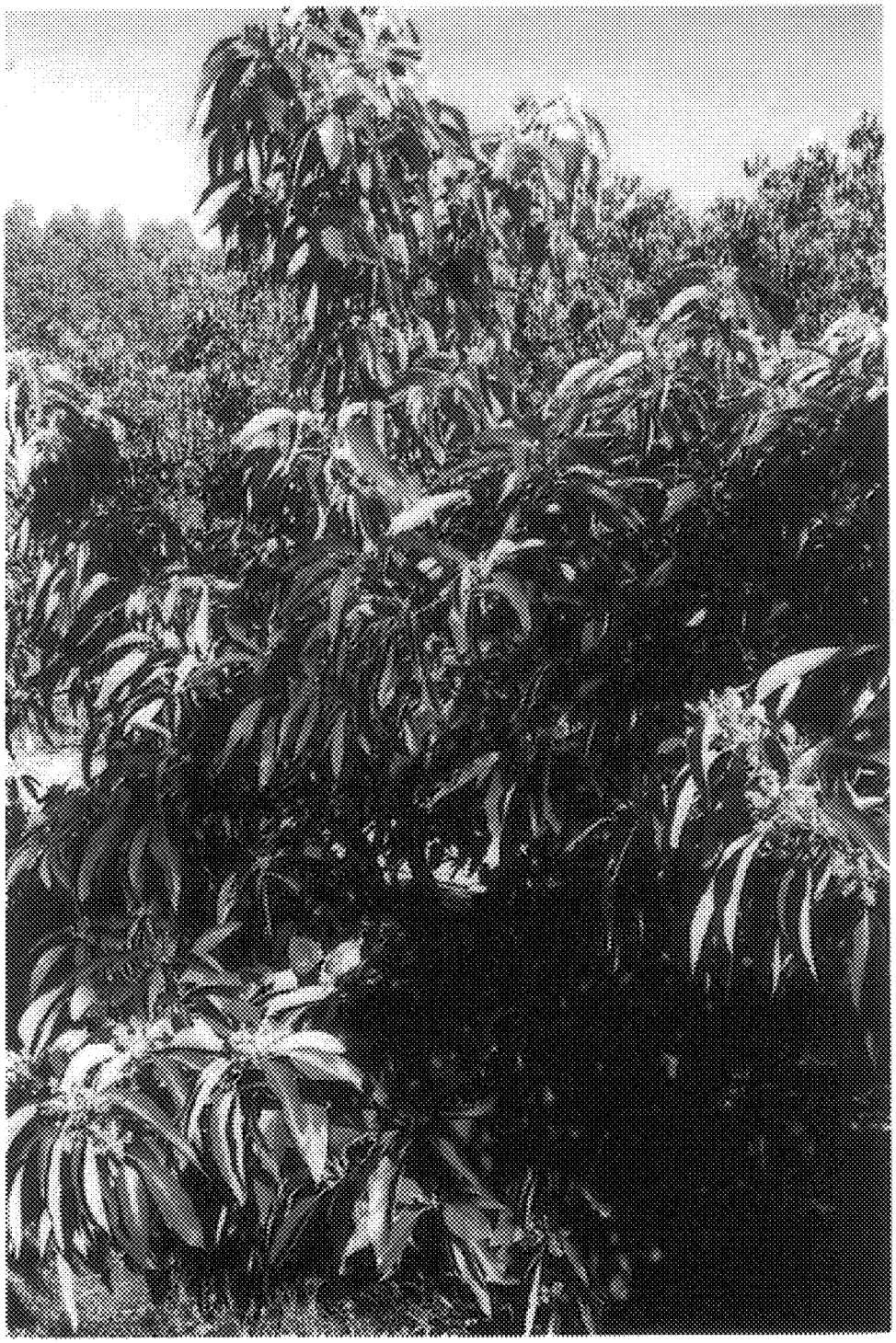
FIG. 2 shows a 4-year old tree of the new variety.
Figure 3:
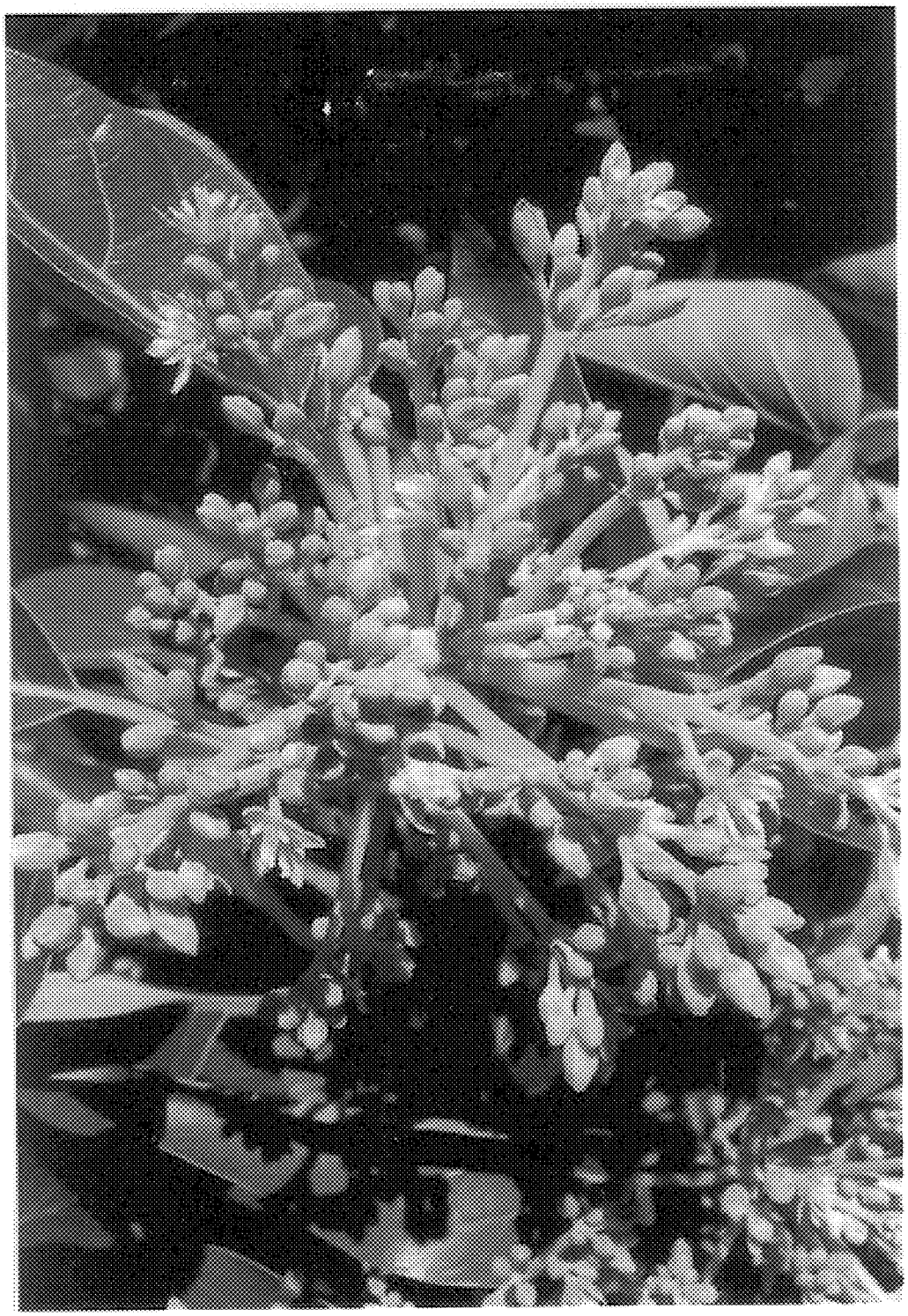
FIG. 3 shows the flowers and buds of the new variety.

The new variety 'LLANOS HASS' is vigorous, upright with a medium to large height. Anthocyanin is not present in the stems of young shoots. The leaflets are large, horizontal, long and narrow with blades folding concave with a lanceolate shape. The tips of the leaflets are acute and anthocyanin is present in newly emerged leaves. The following description is of 2 to 5 year-old plants grown in Kwinana, Hope Valley, Western Australia with color descriptions in accordance with The Color Chart of The Royal Horticultural Society, London (3$^{rd}$ ed. 1995). The plants described were grafted in 1996 onto rootstock as previously described.

All dimensions are in millimeters, weights in grams (unless otherwise stated).

COMPARATIVE TRIAL

Comparison variety: 'HASS'.

Location: Kwinana, Hope Valley, Western Australia (Zone 50) approximately 30 Km south of Perth.

Condition: Scion wood from the original 'LLANOS HASS' seedling tree was grafted onto Guatemalan seedling rootstocks, trees were planted in 1996 at spacings of 5.0 m ×2.5 m to a total of 100 trees. 'HASS' trees grafted onto Guatemalan seedling rootstocks were planted randomly within the 'LLANOS HASS' block in 1997 to a total of 10 trees. The plants were grown in the field, soil being deep sands; all trees were managed in the same manner with regard to irrigation and nutrition. Irrigation using mini sprinklers aimed to wet 100% of soil in the drip zone. Nutrition requirements were based on annual leaf analysis and applied by fertigation.

Trial design: The trial set up was of a completely randomized design.

Measurements: Samples were randomly collected from trees selected at random for analysis.

LLANOS HASS CHARACTERISTICS

Plant: Habit vigorous, upright.
*Height.*—About 3 meters (3 year-old tree).
*Spread.*—About 2 meters.
Trunk diameter: About 50 mm at 1 meter high.
Bark color: Green, near 139B. Texture: Smooth.
Branch size: At 1 meter: about 1600 mm long:30 mm diameter at sight of trunk.
Stem: Anthocyanin not present in young shoots.
Leaf: Large size (183 mm×71 mm), shape lanceolate (length/width ratio about 2.6).
*Attitude.*—Horizontal, blade folding concave.
*Length.*—Long; about 17 cm to about 20 cm.
*Width.*—Narrow; about 5.5 cm to about 6.5 cm.
*Tip.*—Acute, anthocyanin present in newly emerged leaves, anise aroma not present when crushed.
*Shape of leaf base.*—Obtuse.
*Margin.*—Smooth and uniform.
*Texture.*—Smooth.
*Color.*—Top, green, near 137B; underside, yellow-green, near 146C.
*Venation.*—Pinnate.
*Vein color.*—Yellow-green, near 145A.
*Petiole.*—Average length is 42 mm; diameter, 3 to 4 mm; color, yellow-green, near 145A.
Inflorescence:
*Flower.*—Type 'B';[1] habit late.
*Bud.*—Color, yellow, near 13B; length, about 8 mm; diameter, about 4 mm; shape, rounded base, acute tip.
*Petal.*—Color is yellow, near 9B; length, about 6 mm; width, about 2 mm; margin, smooth and uniform; texture, smooth; number of petal, 6; shape, apex acute, base flattened.
*Reproductive organs.*—Short, about 6 to 10 cm, tightly packed flower stalks (peduncles) and giving the appearance of higher density of flowers as compared to 'HASS'; color yellow, near 9B.
*Flower pedicel.*—Length, about 4 to 5 mm; diameter, about 2 mm; color yellow-green, near 145B.
Mature fruit: Early maturing, size small (97 mm×64 mm); shape pyriform; base rounded, stylar region slightly depressed; length: diameter ratio (1.5:1), stalk cavity present, relief of surface rough.
*Pedicel.*—Average length, about 20 mm; average diameter, about 9 mm.
*Peduncle.*—Average length, about 80 mm; average diameter, about 6 mm; shape, cylindrical, nailhead.
Ripe fruit[2]: Color of skin purple black, thickness of skin thick (1.75 mm), texture of skin leathery, adherence of skin to flesh medium, peels easily with no cracking unless over-mature; main flesh color yellow, wide green layer of flesh next to skin, fibers in flesh inconspicuous, flesh texture smooth, seed set into cavity tight.
Seed: Seed: size compared to fruit large (flesh weight:seed weight ratio 3.7:1), shape in longitudinal section base flattened, ovate, apex conical. Weight, about 37 g; length, about 45 mm; diameter, about 40 mm. Color light brown, near 165A.
Fruit weight: Characteristic and observed fruit weight: average of 207 g (SD 27); however, fruit size depended on the crop load on young trees.
Pollination requirements: The 'ILLANOS HASS' variety has displayed the ability to be self-fertile. Known pollinators that stimulate the best fruit set are those of the "A" type pollinator variety.[1] No known pollinators are incompatible with the 'LLANOS HASS' variety.
Productivity: One hundred trees were tested, spaced 5.0 m×2.5 m; fruit picked averaged 32 kg per tree at age 3 years.
Market use: Market use of fruit of observed plant: Avocados are washed, polished sized & packed in cardboard stackable boxes and transported to markets or can be bulk packed in crates and sent to packing houses for distribution to wholesalers/markets. Avocados can be refrigerated and can also be artificially ripened by gassing. Natural ripening takes between 6–10 days after picking. The rough, thick skin is a good protection for the flesh when being handled, either by picking, packing or transporting. Many people use avocado in place of butter as it has no cholesterol and full of the oils that are good for one's health. Avocados are recommended by the Heart Foundation. They are also used in fresh salads, dips, sauces and with seafood and meat dishes. Avocado is not used cooked as it becomes bitter when heated.
Plant/fruit disease resistance/susceptibility:
*Plant diseases.*—Most avocado plants are susceptible to Phytophthora (root rot). However in the past 7 years there has not been any evidence of the variety LLANOS HASS being attacked by this disease. Good drainage, canopy management and use of good rootstock is paramount in keeping this disease at a minimum. Some growers spray or inject chemicals such as phosphonate, into the trunk. No chemicals have been used during the 7 years cultivating this new variety other than fertilizers through a fertigation system.
*Fruit diseases.*—Susceptible to Anthracnose and certain pests such as fruit fly and scale. Safe foliar sprays are effective for pests. Fruit can be dipped or sprayed with specific, legal chemical for anthracnose.
Winter hardines and drought/heat tolerance: Both Plant and Fruit can withstand light frosts (3–5 degrees C.) during winter. During hot summers (as high as 38 degrees C.), as long as the plant gets adequate water usually twice per day, it will survive, however the fruit require adequate foliage to protect them from burning.
First/last picks: Characteristics and observed date of first and last pick in the specified location of culture: In Western Australia the date of first pick is the 1st week in May and last pick can be left as late as end of July. Fruit seem to start turning purple-black on the tree during this last month. Dry matter percentages increase the longer the fruit is left on the tree. Acceptable percentages vary from country to country, but in Australia the minimum is 21%.

[1]Type A and Type B relates to the floral behavior classification. A type varieties first open during the morning when their stigmas are receptive (female stage), then close about noon. The flowers remain closed until noon of the following day, then re-open and release their pollen (male stage). B type varieties open first in their female receptive stage in the afternoon, closing overnight, and re-opening the following morning, when their pollen is released.

[2]Mature fruit is defined as fruit that has attained a specific percentage of dry matter/oil content and is ready to harvest from the tree. Ripe fruit is defined as fruit that is mature and is soft and ready to eat after being picked off the tree. Avocados ripen after being picked from the tree.

COMPARISON OF PERSEA VARIETIES

| | 'LLANOS HASS' | 'HAAS' |
|---|---|---|
| YOUNG SHOOT | | |
| Color | green | green |
| Anthocyanin coloration | absent | absent |
| Color of lenticels | red | green |
| Size of lenticels | about 1 to 2 mm in length and about 1 mm in width | about 1 to 2 mm in length and about 1 mm in width |
| YOUNG LEAF: | | |
| Anthocyanin coloration | present | present |
| Color of petiole pubescence | white | white |
| LEAF: | | |
| Attitude | horizontal | horizontal |
| Blade/folding | concave | concave |
| Blade size | large | large |
| Blade Length (mm) | | |
| Mean | 183 | 165 |
| Std. Deviation | 21 | 25 |
| LSD/sig | 9 | pS0.01 |
| Blade Width (mm) | | |
| Mean | 71 | 76 |
| Std. Deviation | 10 | 9 |
| LSD/sig | 4 | pS0.01 |
| Blade Length/Width Ratio | | |
| Mean | 2.6 | 2.2 |
| Std. Deviation | 0.3 | 0.4 |
| LSD/sig | 0.1 | PS0.01 |
| Blade shape | lanceolate | elliptical |
| Blade - shape of tip | acute | acute |
| Blade undulation of margin | weak | weak |
| Blade anise aroma | absent | absent |
| Inflorescence: | | |
| Length of Axis | medium | long |
| Color of Lenticels | green | green |
| Flowering type | Type B | Type A |
| Flower: | | |
| Pubescence of sepal | present | present |
| Reproductive Organs | short, about 6 to 10 cm, tightly packed flower stalks (peduncles) compared to 'HASS'; appears to have a higher density of flowers than 'HASS'; color yellow, near 9B | long, about 12 to 14 cm; color yellow, near 9B |
| Mature fruit: | | |
| Size | small | small |
| Length (mm) | | |
| Mean | 97 | 100 |
| Std. Deviation | 10 | 11 |
| LSD/sig | 7.0 | ns |

-continued

COMPARISON OF PERSEA VARIETIES

| | 'LLANOS HASS' | 'HAAS' |
|---|---|---|
| Diameter (widest point - mm) | | |
| Mean | 64 | 66 |
| Std. Deviation | 6 | 7 |
| LSD/sig | 4.0 | ns |
| Length/Diameter ratio | | |
| Mean | 1.5 | 1.5 |
| Std. Deviation | 0.1 | 0.1 |
| LSD/sig | 0.1 | ns |
| Shape of basal part of fruit | rounded | rounded |
| Stalk cavity | present | present |
| shape of sytlar region | slightly depressed | slightly depressed |
| Relief of surface | rough | rough |
| Pedicel: | | |
| Length | medium | medium |
| Shape | cylindrical | cylindrical |
| "Nailhead" Shape | present | present |
| color | green | yellow/green |
| Pedicel Length | | |
| Mean | 81 | 123 |
| Std. Deviation | 15 | 33 |
| LSD/sig | 13.8 | PS0.01 |
| Ripe fruit: | | |
| Color of skin | purple black | purple black |
| Thickness of skin (mm) | thick | thick |
| Mean | 1.75 | 1.42 |
| Std. Deviation | 0.16 | 0.22 |
| LSD/sig | 0.20 | pS0.01 |
| Texture of skin | leathery | corky |
| Adherence of skin to flesh | medium | medium |
| Main color of flesh | yellow | yellow |
| Color of flesh next to skin | green, near 143A | green |
| Width of colored layer of flesh next to skin | wide, near 5 mm | medium |
| Texture of flesh | smooth | smooth |
| Firmness of flesh | medium | medium |
| Anise aroma of flesh | absent | absent |
| Setting of seed in cavity | tight | tight |
| Seed size compared to fruit size | large | medium |
| Flesh: seed to weight ratio | | |
| Mean | 3.7 | 4.8 |
| Std. Deviation | 0.6 | 1.0 |
| LSD/sig | 0.5 | PS0.01 |
| Seed: shape in longitudal section | base flattened, apex conical | ovate |
| Weight: | 37 g | 29 g |
| Length: | 45 mm | 47 mm |
| Diameter: | 40 mm | 33 mm |
| Color: | light brown, near 165A | same |
| Time of flowering: | late | late |
| Time of fruit maturity for harvesting: | early | late |

We claim:

1. A new Avocado plant of the variety substantially as shown and described.

* * * * *